United States Patent
Shiono et al.

(10) Patent No.: US 8,097,137 B2
(45) Date of Patent: Jan. 17, 2012

(54) GAS SENSOR ELEMENT AND GAS SENSOR

(75) Inventors: Koji Shiono, Aichi (JP); Kunio Imai, Gifu (JP)

(73) Assignee: NGK Spark Plug Co., Ltd. (JP)

( * ) Notice: Subject to any disclaimer, the term of this patent is extended or adjusted under 35 U.S.C. 154(b) by 436 days.

(21) Appl. No.: 12/204,947

(22) Filed: Sep. 5, 2008

(65) Prior Publication Data
US 2010/0059374 A1    Mar. 11, 2010

(51) Int. Cl.
*G01N 27/406* (2006.01)
(52) U.S. Cl. ....... 204/424; 204/426; 204/428; 73/23.31; 73/23.32; 205/783.5; 205/785
(58) Field of Classification Search .......... 204/424–429; 73/23.31–23.32; 205/783.5–785, 781
See application file for complete search history.

(56) References Cited

U.S. PATENT DOCUMENTS

| | | | | |
|---|---|---|---|---|
| 4,328,296 A | * | 5/1982 | Tanaka et al. | 429/304 |
| 2002/0108856 A1 | * | 8/2002 | Kunimoto et al. | 204/425 |
| 2004/0035700 A1 | * | 2/2004 | Taguchi et al. | 204/429 |
| 2004/0084309 A1 | * | 5/2004 | Ando et al. | 204/426 |

FOREIGN PATENT DOCUMENTS

| | | |
|---|---|---|
| JP | 56093039 | 7/1981 |
| JP | 56160653 | 12/1981 |
| JP | 8022820 | 1/1996 |
| JP | P11230930 | 8/1999 |

* cited by examiner

*Primary Examiner* — Keith Hendricks
*Assistant Examiner* — Bach Dinh
(74) *Attorney, Agent, or Firm* — Kusner & Jaffe

(57) ABSTRACT

To provide a gas sensor element having a base body whose durability is unlikely to deteriorate during the use and exhibiting excellent endurance and responsiveness.

[Means for Solution] A gas sensor element 2 comprising: a closed-bottomed cylindrical base body 28 made of solid electrolyte which contains zirconia as a principal component; an outer electrode 26 formed on an outer surface of the base body 28; an inner electrode 27 formed on an inner surface of the base body 28; and an adhesive layer 29 formed between the base body 28 and the outer electrode 26 and containing zirconia as a principal component, wherein a proportion of tetragonal in zirconia particles of the base body 28 falls within the range from 45% or more to 60% or less and, wherein a proportion of tetragonal in zirconia particles of the adhesive layer 29 is greater than that of tetragonal in zirconia particles of the base body 28.

8 Claims, 5 Drawing Sheets

GAS SENSOR ELEMENT AND GAS SENSOR

FIELD OF THE INVENTION

The present invention relates to a gas sensor element comprising: an outer electrode formed, through an adhesive layer, on an outer surface of a closed-bottomed cylindrical base body which is made of solid electrolyte containing zirconia as a principal component; an inner electrode formed on an inner surface of the base body, and wherein an electrical characteristic value measured between the electrodes varies according to a component of gas to be detected. The present invention also relates to a gas sensor which employs such a gas sensor element therein.

BACKGROUND OF THE INVENTION

A conventional gas sensor is comprised of an outer electrode (detection electrode) formed on an outer surface of a closed-bottomed cylindrical base body which is made of solid electrolyte and an inner electrode (reference electrode) formed on an inner surface of the base body. Electromotive force generated in the solid electrolyte, which serves as the base body, is taken out from the outer electrode and the inner electrode to thereby detect oxygen concentration or the like.

There has been a demand that the outer electrode of such a gas sensor element is required not to be peeled off from a base material, even when the outer electrode is exposed for a long period of time to a high temperature gas to be detected. In order to fulfill such a demand, there have been proposed various methods, for example, a method wherein the outer surface of the base body is roughened by etching process or the like, and a method wherein a porous layer or projections is/are formed on the outer surface of the base body before or after sintering the base body.

For example, a conventionally known method for forming projections on the outer surface of the base body is that adhesive particles comprised of: granules more than half of which are occupied by particles having a particle size of 44 micrometers or more; and fine particles having a size of 10 micrometers or less, are applied to the base body, and thereafter they are simultaneously sintered. In this way, peeling of the outer electrode can be effectively prevented. See, for example, Patent Document 1, Japanese Patent Application Laid-Open (kokai) No. S56-160653.

Further, when such projections are formed, water vapor tends to enter a gap between neighboring projections and causes a phase transition of zirconia. The projections change in volume on a microscopic scale, causing the formation of minute cracks. As a result, the projections break away from the base body, causing a crack failure. In order to prevent such crack failure, it has been disclosed that the projections are formed into a single layer, the area occupied by the projections accounts for 10 to 85%, and a distance between the neighboring projections is 5 to 40 micrometers. See, for example, Patent Document 2, Japanese Patent Application Laid-Open (kokai) No. H11-230930.

SUMMARY OF THE INVENTION

A base body constituting a gas sensor element tends to be weak and fragile due to a phase transition of zirconia that is a principal component of the base body. More particularly, although zirconia constituting the base body has a cubic and tetragonal structure at an initial stage, the tetragonal phase is converted to the monoclinic phase during the use of the gas sensor element. When the tetragonal phase is transformed to the monoclinic phase, durability of the base body deteriorates due to volume expansion whereby the base body becomes fragile.

In order to prevent the deterioration in durability of the base body, it is possible to reduce the content of tetragonal, which transforms into monoclinic, in zirconia of the base body. However, the toughness of the base body lowers when the content of tetragonal in zirconia is reduced, which is not desirable.

Further, the projections formed on the outer surface of the base body generally have a similar phase structure as that of the base body. Thus, when the content of tetragonal in zirconia particles of the base body is reduced as described above, the content of tetragonal in zirconia particles of the projections is also reduced, resulting in impairing the responsiveness of the gas sensor element.

The present invention has been accomplished in view of the foregoing problems, and an object of the present invention is to provide a gas sensor element having a base body whose durability is unlikely to deteriorate during the use and exhibiting excellent endurance and responsiveness. Another object of the present invention is to provide a gas sensor employing such a gas sensor element.

DETAILED DESCRIPTION OF PREFERRED EMBODIMENT

A gas sensor element comprising: a closed-bottomed cylindrical base body made of solid electrolyte which contains zirconia as a principal component; an outer electrode formed on an outer surface of the base body; an inner electrode formed on an inner surface of the base body; and an adhesive layer formed between the base body and the outer electrode and containing zirconia as a principal component, wherein a proportion of tetragonal in zirconia particles of the base body falls within a range from 45% or more to 60% or less and wherein a proportion of tetragonal in zirconia particles of the adhesive layer is greater than that of tetragonal in zirconia particles of the base body.

In the gas sensor element according to the present invention, the proportion of tetragonal in zirconia particles of the adhesive layer is preferably 60% or more. Further, the base body preferably contains alumina of 5% by weight or more. Furthermore, an average particle size of alumina contained in the base body is preferably 1 micrometer or less.

Moreover, a gas sensor according to the present invention comprising a gas sensor element and a metal shell which surrounds the gas sensor element, wherein the gas sensor employs the gas sensor element according to the present invention.

According to the present invention, there is provided a gas sensor element in which a proportion of tetragonal in zirconia particles of a base body falls within a range from 45% or more to 60% or less, and wherein a proportion of tetragonal in zirconia particles of an adhesive layer is greater than that of tetragonal in zirconia particles of the base body. Thus, it is possible to prevent deterioration in durability of the base body during the use and provide an excellent endurance and responsiveness.

Figure 1:
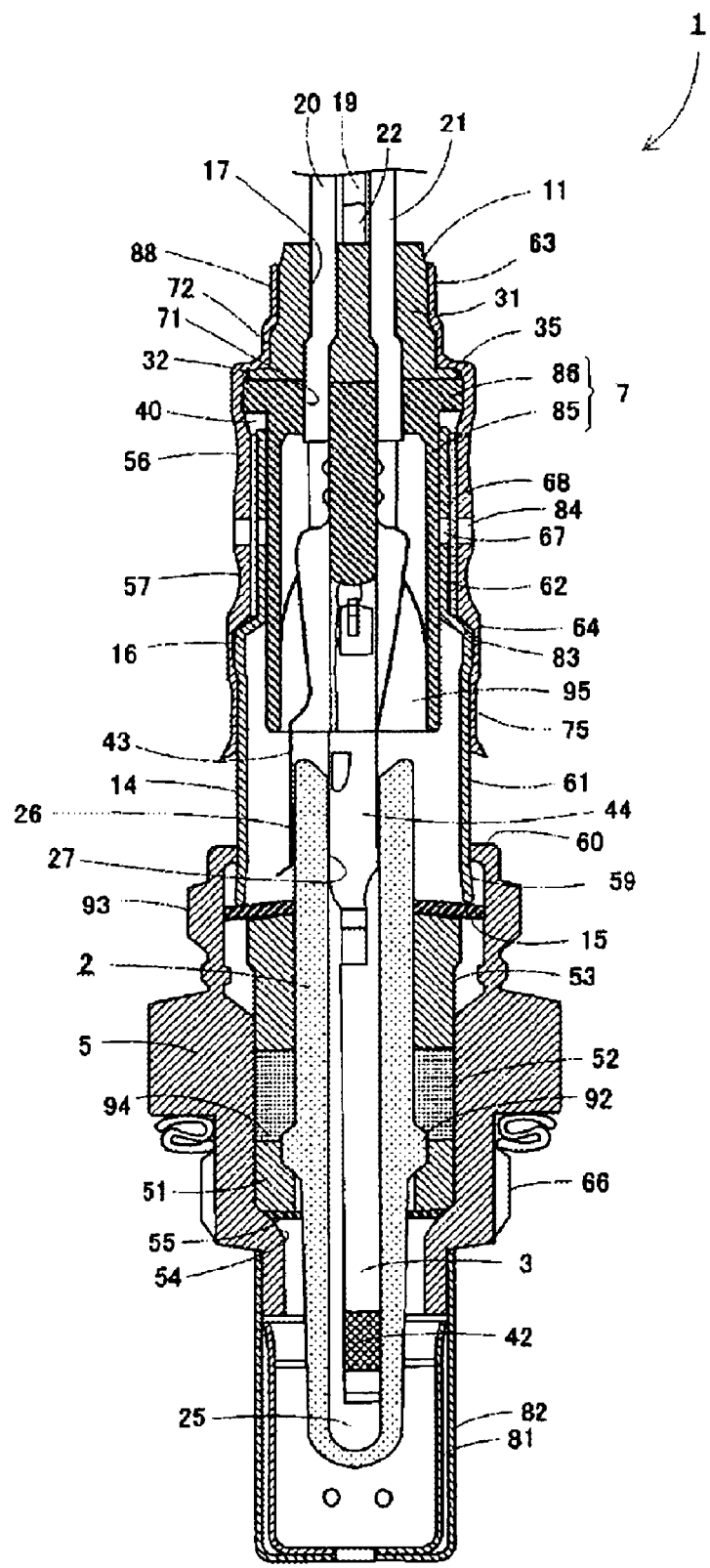
FIG. 1 is a sectional view showing an example of a gas sensor according to the present invention.
Figure 2:
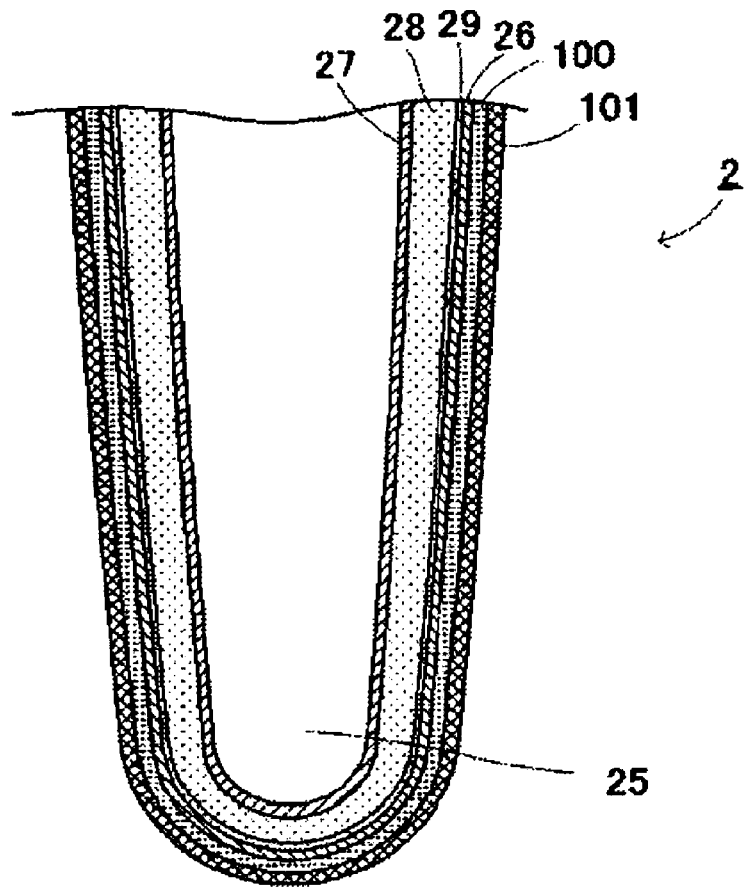
FIG. 2 is a sectional view showing a front end portion of a gas sensor element according to the present invention.
Figure 3:
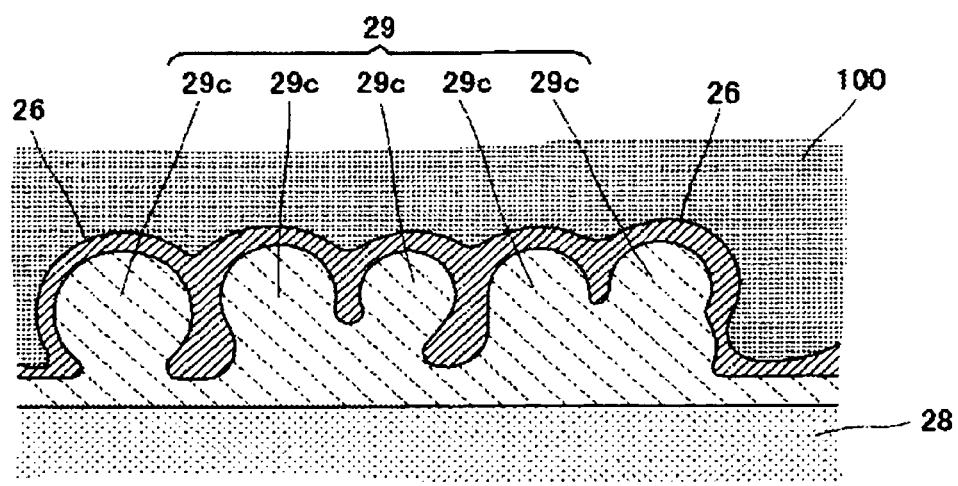
FIG. 3 is an enlarged sectional view of a base body and an adhesive layer of a gas sensor element.

Hereafter, the embodiment of a gas sensor according to the present invention will be described with reference to the drawings. In this embodiment, a gas sensor (oxygen sensor) mounted in an exhaust pipe of a car and detecting a concentration of oxygen in exhaust gas will be described. FIG. 1 is a sectional view showing an example of a gas sensor according to the present invention. FIG. 2 is a sectional view showing a front end portion of a gas sensor element 2 used in the gas sensor according to FIG. 1. FIG. 3 is an enlarged sectional view of the gas sensor element 2 shown in FIG. 2.

As shown in FIG. 1, the gas sensor 1 is comprised of the closed-bottomed cylindrical gas sensor element 2 having a closed front end, a ceramic heater 3 inserted into a closed-bottomed hole 25 of the gas sensor element 2, and a metal shell 5 holding the gas sensor element 2 therein. In the following, in an axial direction of the gas sensor element 2 in FIG. 1, a side towards a front end portion which is to be exposed to a measuring gas (exhaust gas) is regarded as a "front end side" (a closed end at lower direction in FIG. 1), and an opposite side thereto is regarded as a "rear end side" (upper direction in FIG. 1).

As shown in FIG. 2, the gas sensor element 2 is comprised of: a base body 28 made of a closed-bottomed cylindrical solid electrolyte that has an oxygen ion conductivity and mainly contains partially stabilized zirconia in which yttria is dissolved as a stabilizing agent; a porous inner electrode 27 made of Pt or Pt alloy and formed on an inner surface of the closed-bottomed hole 25 of the base body 28 so as to cover the whole inner surface; and a porous outer electrode 26 formed on an outer surface of the base body 28 through an adhesive layer 29 having a roughened structure (also see FIG. 3).

As shown in FIG. 1, an engaging flange portion 92 that radially outwardly projects is formed in a position generally center of the gas sensor element 2 in its axial direction. Further, the rod-like shaped ceramic heater 3 has therein a heating element 42 including a heat resistant element. The ceramic heater 3 is electrically connected through leads for heater 19, 22 (this will be described in greater detail below) so as to heat the heating element 42, resulting in energizing the gas sensor element 2.

The metal shell 5 is comprised of a thread portion 66 for mounting the gas sensor 1 on a mounting portion of an exhaust pipe and a hexagonal portion 93 engaging with a mounting tool when mounting the gas sensor 1 on the fitting portion of the exhaust pipe. Further, the metal shell 5 is configured so that an aluminum support member 51 that holds the gas sensor element 2 from the front end side, a talcum filler 52 disposed on the rear end side of the support member 51 and an aluminum sleeve 53 pressing the filler 52 towards the front end side from the rear end side are accommodated therein.

In the metal shell 5, a metal fitting side step portion 54 radially projecting towards a front end side inner circumference is formed to thereby lock the support member 51 through a packing 55. In addition, the metal shell 5 holds the gas sensor element 2 in such a manner that the support member 51 supports the engaging flange portion 92 through a packing 94. The filler 52 is disposed between the inner surface of the metal shell 5 and the outer surface of the gas sensor element 2 on the rear end side of the support member 51. Further, the sleeve 53 and an annular ring 15 are coaxially disposed in this order on the rear end side of the filler 52.

Furthermore, inside of the metal shell 5 on the rear end side, a front end side of an inner housing member 14 made of SUS 304L is disposed. The inner housing member 14 is fixed in the metal shell 5 by inwardly caulking a metal fitting side rear end portion 60 of the metal shell 5 towards the front end side in a state where an opening end portion (a front end opening end portion 59) having a larger diameter at the front end side is brought into contact with the annular ring 15. In addition, in the gas sensor 1, the filler 52 is compressed and filled through the sleeve 53 by caulking the metal fitting side rear end portion 60 of the metal shell 5. As a result, the gas sensor element 2 is held in an airtight manner in the cylindrical metal shell 5.

The inner housing member 14 is comprised of: an inner housing step portion 83 formed in the generally central region of the inner housing member 14 in the axis direction; an inner housing front end side drum section 61 formed on the front end side with respect to the inner housing step portion 83; and a rear end side drum section 62 formed on the rear end side with respect to the inner housing step portion 83. The rear end side drum section 62 has inner and outer diameters smaller than those of the inner housing front end side drum section 61. The inner diameter of the rear end side drum section 62 is slightly larger than an outer diameter of a separator main body 85 of a separator 7, which will be described in greater detail below. Further, in the rear end side drum section 62, a plurality of air communication holes 67 with a predetermined gap therebetween is formed along the circumferential direction thereof.

The outer housing member 16 assumes a cylindrical shape and formed by a deep-drawing of a SUS304L plate. An outer housing member 16 is constituted by an outer housing rear end side portion 63 at the rear end side thereof where an opening for communicating between the inside and the outside is formed; an outer housing front end side portion 64 at the front end side thereof which is coaxially connected to the inner housing member 14 from the rear end side; and an outer housing step portion 35 connecting the outer housing rear end side portion 63 and the outer housing front end side portion 64. It is noted that a caulking portion 88 for fixing an elastic seal 11 in the airtight manner is formed in the outer housing rear end side portion 63.

Moreover, on the front end side outer circumference of the metal shell 5, double protectors 81 and 82 made of metal and having a plurality of gas introduction holes are formed so as to cover the front end portion of the gas sensor element 2 projecting from the front end of the metal shell 5.

Furthermore, a cylindrical filter 68 for rejecting permeation of water from the air introduction hole 67 is formed outside of the inner housing rear end side drum section 62 of the inner housing member 14. In addition, the filter 68 is a water repellent filter for rejecting permeation of liquid with water as a main component and allowing gases of air or the like to pass through, such as made of a porous fiber structure of a polytetrafluoroethylene (e.g., Goretex (Japan Goretex (kabu)) as a trade name)

The outer housing front end side portion 64 of the outer housing member 16 is formed so as to cover the inner housing member 14 in which the filter 68 is disposed (more particularly, the inner housing rear end side drum section 62) from the outside. Further, a plurality of air introduction holes 84 is formed in the outer housing front end side portion 64 in a position corresponding to the filter 68 with a predetermined gap therebetween.

It is noted that the outer housing member 16 and the inner housing member 14 are fixed by a first caulking portion 56 and a second caulking portion 57. The first caulking portion 56 is formed in such a manner that at least a portion of the outer housing front end side portion 64 of the outer housing member 16 at the rear end side with respect to the air introduction hole 84 is radially inwardly caulked through the filter 68. The second caulking portion 57 is formed in such a manner that at least a portion of the outer housing front end side portion 64 of the outer housing member 16 at the front end side with respect to the air introduction hole 84 is radially inwardly caulked through the filter 68. At this time, the filter 68 is held in airtight manner between the outer housing member 16 and the inner housing member 14. Further, the outer housing front end side portion 64 of the outer housing member 16 is disposed so as to overlap the inner housing front end side drum section 61 from the outside. At least a portion of the overlapped portion is inwardly caulked in the circumferential direction to thereby form a coupled caulking portion 75.

Thereby, the air as a reference gas is introduced into the inner housing member 14 through the air introduction hole 84, a filter 68 and the air introduction hole 67, and further introduced into the closed-bottomed hole 25 of the gas sensor element 2. On the other hand, since water droplet cannot pass the filter 68, a permeation of the water into the inner housing member 14 is prevented.

The elastic seal member 11 is fitted in the outer housing member 16 on the rear end side (outer housing rear end side portion 63). The seal member 11 has four lead insertion holes 17 that penetrate from the front end side to the rear end side. Those insertion holes 17 are formed for inserting leads for element 20 and 21 electrically connected to the gas sensor element 2 and the leads for heater 19 and 22 electrically connected to the ceramic heater 3.

Moreover, the separator 7 disposed so that the front end side thereof enters the inner housing rear end side drum section 62 of the inner housing member 14 has separator lead insertion holes 71 penetrating from the front end side to the rear end and formed for inserting the leads for element 20 and 21 and the leads for heater 19 and 22 therein. Further, a closed-bottomed holding hole 95 opening at the front end face is formed in the separator 7 in the axis direction. In the holding hole 95, the rear end portion of the ceramic heater 3 is inserted so as to come in contact with the bottom face of the holding hole 95, thereby aligning a position of the ceramic heater 3 in the axis direction with respect to the separator 7.

The separator 7 has the separator main body 85 inserted in the inner housing member 14 at the rear end side and a separator flange portion 86 extending outwardly in the circumferential direction from the rear end portion of the separator main body 85. That is, the separator 7 is disposed in the outer housing member 16 in the state where the separator main body 85 enters in the inner housing member 14 while the separator flange portion 86 is supported by the rear end face of the inner housing member 14 through an annular seal member 40 made of fluorocarbon rubber.

Moreover, the leads for element 20 and 21 and the leads for heater 19 and 22 are pulled out from the inner housing member 14 and the outer housing member 16 to the outside through the separator lead insertion holes 71 of the separator 7, and the lead insertion holes 17 of the elastic seal member 11. In addition, these four leads 19, 20, 21 and 22 are connected to an external connector, which is not illustrated. Input and output of an electric signal between an external apparatus, such as an ECU, and each lead 19, 20, 21 and 22 is conducted through the connector.

Moreover, although the details of the each lead 19, 20, 21 and 22 are not illustrated, the leads 19, 20, 21 and 22 are formed from a conductive wire covered with a resin insulating film, and the rear end side of the conductive wire is connected to a connector terminal of the connector. The front end side of the conductive wire of the lead for element 20 is caulked with the rear end portion of the terminal metal fitting 43 which is fitted onto the outer face of the gas sensor element 2. The front end side of the conductive wire of the lead for element 21 is caulked with the terminal metal fitting 44 which is press fitted to the inner face of the gas sensor element 2. In this way, the lead for element 20 is electrically connected with the outer electrode 26 of the gas sensor element 2, and the lead for element 21 is electrically connected with the inner electrode 27. On the other hand, the front end portions of conductive wires of the leads for heater 19 and 22 are connected with a pair of heater terminal fitting, respectively, which is joined to a heat resistant element of the ceramic heater 3.

At the rear end side of the separator 7, the elastic seal member 11 made of fluorocarbon rubber or the like which is excellent in heat resistance is fixed in the outer housing member 16 by caulking the outer housing member 16 to form the caulking portion 88. The elastic seal member 11 is comprised of a main body portion 31 and a sealing member flange 32 radially outwardly extending from the side circumferential face of the main body portion 31 at the front end side. Then, four lead insertion holes 17 are formed so as to penetrate the main body portion 31 in the axis direction.

Next, the gas sensor element 2 which is the principal part of the invention will be described. As shown in FIG. 2, the gas sensor element 2 is comprised of: the base body 28; the inner electrode 27 formed on the inner surface of the closed-bottomed hole 25 of the base body 28 so as to cover the whole inner surface; and the outer electrode 26 formed on the outer surface of the base body 28 through the adhesive layer 29 having a roughened structure. As shown in FIG. 3, the adhesive layer 29 is comprised of a plurality of convex portions 29c and a plurality of concave portions formed therebetween. Further, as shown in FIG. 2, a porous electrode protection layer 100 is formed on the entire outer electrode 26, and furthermore, a poisoning protection layer 101 is formed on the electrode protection layer 100.

The base body 28 of the gas sensor element 2 is made of a solid electrolyte containing zirconia as a principal component, and alumina ($Al_2O_3$), silica ($SiO_2$) or the like is added thereto, if necessary. Moreover, the adhesive layer 29 is also made of a solid electrolyte containing zirconia as a principal component, and alumina ($Al_2O_3$), silica ($SiO_2$) or the like is added thereto, if necessary.

The gas sensor element 2 of the invention is characterized by the fact that a proportion of tetragonal in zirconia particles of the base body 28 falls within a range from 45% or more to 60% or less and that a proportion of tetragonal in zirconia particles of the adhesive layer 29 is greater than that of tetragonal in zirconia particles of the base body 28.

When the proportion of tetragonal in zirconia particles of the base body 28 exceeds 60%, the phase transition from tetragonal phase to monoclinic increases and the durability of the base body deteriorates when the gas sensor element 2 is assembled in the gas sensor 1. On the other hand, when the proportion of tetragonal in zirconia particles of the base body 28 is less than 45%, toughness of the base body 28 falls at an initial stage. That is, when the proportion of tetragonal in the base body 28 falls within the range from 45% or more to 60% or less, it is possible to secure the toughness of the base body 28 at the initial stage and to prevent the deterioration in durability thereof during the use.

In the present invention, since the content of tetragonal in zirconia particles of the adhesive layer 29 is greater than that of tetragonal in zirconia particles of the base body 28, an impairment of the responsiveness, which is an electrical property, can be prevented. Thus, when the content of tetragonal in zirconia in the adhesive layer 29 is increased, as described above, a crack or the like is likely to occur due to volume expansion along with the phase transition from tetragonal to monoclinic. However, since the surface area of the adhesive layer 29 increases due to the crack or the like, it is rather preferable to increase double phase interface, which contributes to the responsiveness.

The proportions of tetragonal (T phase [%]) in zirconia particles of both base body 28 and the adhesive layer 29 can be calculated by a fraction of the integrated intensity of the spectrum of tetragonal (T phase) and cubic (C phase) analyzed by an X-ray diffraction. The proportion of tetragonal can be calculated by the following expression (1):

Equation 1

$$TPhase[\%] = \frac{T(004) + T(400)}{T(004) + C(400) + T(400)} \times 100 \quad (1)$$

where T (004) and T (400) represent an integrated intensity of a face (004) and a face (400) of the T phase, and where C (400) represents an integrated intensity of a face (400) of the C phase.

In addition, although the proportion of tetragonal in zirconia particles of the base body 28 or the adhesive layer 29 of the unused gas sensor element 2 should be within the above mentioned range, it is not necessary within the above range after actually using the gas sensor element 2 mounted on the gas sensor 1.

The content of tetragonal in the zirconia particles of the adhesive layer 29 is preferably 60% or more. When the content of tetragonal in zirconia particles of the adhesive layer 29 is less than 60%, the responsiveness, which is an electrical property, may be impaired. The content of tetragonal in zirconia particles of the adhesive layer 29 is preferably 70% or less. When the content of tetragonal in zirconia particles of the adhesive layer 29 exceeds 70%, the adhesive layer 29 is likely to be peeled from the base body 28.

Further, the mean particle size of zirconia particles constituting the base body 28 is preferably 0.6 micrometer or less. Furthermore, the mean particle size of zirconia particles constituting the adhesive layer 29 is preferably 0.5 micrometers or more. When the mean particle size of zirconia particles constituting the base body 28 exceeds 0.6 micrometer, the durability of the base body 28 is likely to deteriorate. When the mean particle size of zirconia particles constituting the adhesive layer 29 is less than 0.5 micrometer, the responsiveness is likely to be impaired, whereby it is not preferable.

It is noted that the mean particle size of zirconia particles is calculated as follows. That is, a polished section face obtained by cutting and grinding the base body 28 or the adhesive layer 29 is observed by a scanning electron microscope (SEM) at a magnification of 1500 times. Then, zirconia particles are sketched based on the SEM image so as to analyze the gross area thereof with an image analysis. Thereafter, the thus-obtained gross area of zirconia particles is divided by the number of zirconia particles to thereby figure out an area (Sz) per a single zirconia particle. A diameter of equivalent circle to the area (Sz) is assumed to be a mean particle size (Dz). This can be expressed by the following expressions (2) and (3).

The area per a single zirconia particle ($S_Z$)=Gross area of zirconia particles/the number of zirconia particles (2).

The mean particle size ($D_Z$) of zirconia particles=$2\sqrt{(S_G/\pi)}$ (3).

Moreover, the base body 28 preferably contains alumina, and the alumina content in the base body 28 preferably falls within the range from 5% by weight or more to 20% by weight or less. When the alumina content in the base body 28 exceeds 20% by weight, the internal resistance becomes high, resulting in lowering an output of the gas sensor 1. When the alumina content in the base body 28 is less than 5% by weight, the phase transition from tetragonal to monoclinic in zirconia particles is easily occur, and durability of the base body 28 is likely to deteriorate. The alumina content in the base body 28 is more preferably 10% by weight or more from a viewpoint of an increase in durability or the like.

Further, the mean particle size of alumina particles of the base body 28 is preferably 1.0 micrometers or less. When the mean particle size of alumina particles of the base body 28 exceeds 1.0 micrometers, the phase transition from tetragonal to monoclinic in zirconia particles is likely to occur whereby the durability may deteriorate during the use.

That is, the phase transition from tetragonal to monoclinic in zirconia particles can be controlled by way of adding alumina in the base body 28 or by reducing the size of alumina particles to be contained. Thus, the base body 28 is prevented from the deterioration in durability during the use and secures an excellent endurance.

Although the adhesive layer 29 may contain or may not contain alumina, the alumina content in the adhesive layer 29 is preferably 20% by weight or less when containing alumina. When the alumina content in the adhesive layer 29 exceeds 20% by weight, there is a possibility that the responsiveness is impaired. The alumina content in the adhesive layer 29 is more preferably 10% by weight or less from a viewpoint of an improvement in the responsiveness.

The mean particle size of alumina particles of the adhesive layer 29 is preferably 0.4 micrometers or more. When the mean particle size of alumina particles of the adhesive layer 29 is less than 0.4 micrometer, the responsiveness is likely to be impaired. The mean particle size of alumina particles of the adhesive layer 29 is more preferably 1.0 micrometer or more from a viewpoint of an improvement in the responsiveness.

It is noted that the mean particle size of alumina particles can be calculated in the similar manner to the mean particle size of the above-mentioned zirconia particles. That is, a polished section face obtained by cutting and grinding the base body 28 or the adhesive layer 29 is observed by a scanning electron microscope (SEM) at a magnification of 1500 times. Then, alumina particles are sketched based on the SEM image so as to analyze the gross area thereof with an image analysis. Thereafter, the thus-obtained gross area of alumina particles is divided by the number of alumina particles to thereby figure out an area ($S_A$) per a single alumina particle. A diameter of equivalent circle to the area ($S_A$) is assumed to be a mean particle size ($D_A$). This can be expressed by the following expressions (4) and (5).

The area per a single alumina particle ($S_A$)=Gross area of alumina particles/the number of alumina particles (4).

Mean particle size ($D_A$) of alumina particles=$2 \times \sqrt{(S_G/\pi)}$ (5).

The porous outer electrode 26 made of Pt or Pt alloy is formed on the surface of the adhesive layer 29. Further, the electrode protection layer 100 made of heat resistant ceramic, such as alumina-magnesia spinel, is formed on the outer electrode 26.

Further, the porous poisoning prevention layer 101 covering the electrode protection layer 100 is formed on the surface of the electrode protection layer 100. The poisoning prevention layer 101 is used for protecting catalyst metallic particles of the electrode protection layer 100 from being exposed to poisoning substances, such as lead, phosphorus or silicon contained in an exhaust gas.

The poisoning prevention layer 101 is made of ceramic that contains, for example, titania powder and ceramic powder other than titania. The titania is excellent in adsorbing a poisoning substance. Thus, the poisoning prevention layer 101 containing titania effectively reacts with poisoning substances, such as phosphorus contained in an exhaust gas, and can protect the outer electrode 26 from being exposed thereto. On the other hand, as the ceramic powder other than titania, it is preferable to use ceramic power, such as spinel or mullite, which is unlikely to contract thermally. By using such ceramic powder, it is possible to prevent the poisoning prevention layer 101 from being peeled from the electrode protection layer 100 due to thermal contraction. As a result, it is possible to achieve an excellent endurance.

The titania powder and the ceramic powder are preferably mixed so that a particle size distribution of primary particles of the titania powder falls within a range from 0.003 micrometers or more to 0.5 micrometer or less at a peek and that of primary particles of the ceramic powder other than titania falls within a range from 15 micrometers or more to 65 micrometers or less at a peek. In this way, the porous poisoning prevention layer 101 having substantial gas permeability and a reliable adsorption of the poisoning substances is achievable.

Next, a method for manufacturing the gas sensor element 2 according to the present invention will be described. First, as a fine base material powder for forming the base body 28 of the gas sensor element 2, a bivalent to trivalent metal oxide, such as yttria, calcia or magnesia, is mixed with zirconia, and the resultant mixture is ground. Thereafter, the resulting mixture is calcined in an electric furnace and is again ground to thereby obtain the fine base material powder made of stabilized or partially stabilized zirconia. In addition, the amount of the bivalent to trivalent metal oxide, such as yttria, calcia or magnesia, which is added to zirconia, is adjusted so that the content of tetragonal in zirconia particles of the base body 28 (sintered body) finally falls within a range from 45% or more to 60% or less. Subsequently, the thus-obtained fine base material powder is pulverized through use of a spray dry or the like. The thus-obtained granules are formed into the base body 28 (non-sintered body) having a generally cylindrical shape by way of a pressure molding method, such as a rubber press.

Separately, a paste for forming the adhesive layer 29 is prepared. The paste is prepared in such a manner that water or a water-soluble binder and the like is added to roughening particles that are used for forming the convex portions 29c in the adhesive layer 29. Except for a mixing ratio, a fine base material powder serving as the roughening particles can be produced in a similar manner to the fine base material powder for forming the base body 28. The fine base material powder serving as the roughening particles is prepared so that the proportion of tetragonal in zirconia particles of the resultant sintered adhesive layer 29 is greater than that of tetragonal in zirconia particles of the base body 28 (sintered body).

Thus, in order for the proportion of tetragonal in zirconia particles of the adhesive layer 29 to be greater than that of tetragonal in zirconia particles of the base body 28, for example, the amount of the bivalent to trivalent metal oxide, such as yttria, calcia or magnesia, added to zirconia of the fine base material powder serving as the roughening powder is lower than the amount of the bivalent to trivalent metal oxide, such as yttria, calcia or magnesia, added to zirconia of the fine base material powder used for forming the base body 28.

The roughening power is preferably comprised of, for example, granules made of the above-mentioned fine base material powder with a particle size of 20 micrometers or more to 100 micrometers or less and fine particles made of the above-mentioned fine base material powder with a particle size smaller than that of the granules. When the granules have the particle size less than the above-mentioned lower limit, it is difficult to form the adhesive layer 29 having an excellent heat resistance on the base body 28. On the other hand, when the granules have the particle size greater than the above-mentioned upper limit, the granules tend to fail in achieving a strong bond with the base body 28.

A method for forming such granules is not particularly limited, but granulation through use of a spray drier stabilizes the shape of granules and produces fine granules. The thus-produced granules exhibit an increased bonding force between the base body 28 and the adhesive layer 29 (convex portion 29c). Therefore, employment of a spray drier for granulation is preferred. Most of the fine particles preferably have a particle size of not greater than 10 µm, more preferably, at least 80% of the fine particles have a particle size of not greater than 2.5 µm. Since the fine particles are used as sintering aids for aiding formation of a bond between the base body 28 and the granules, particles having a relatively large particle size cannot sufficiently yield the required aiding effect.

The paste is applied to the outer surface of the base body 28 (non-sintered body) by immersing the base body 28 (non-sintered body) in the paste or the like. The base body 28 coated with the paste is dried and is then sintered at a temperature of 1400-1600 degrees C. for 1 to 3 hours, for example. Further, an oxidizing atmosphere is usually preferred for sintering. With this sintering, it is possible to obtain the base body 28 in which the adhesive layer 29 containing a plurality of convex portions 29c is formed on the outer surface thereof, and the content of tetragonal in zirconia particles thereof is 45% or more to 60% or less. Further, the content of tetragonal in zirconia particles of the adhesive layer 29 is greater than that of tetragonal in zirconia particles of the base body 28.

Furthermore, the outer electrode 26 made of platinum is formed by vapor deposition or chemical plating or the like on an outer circumferential face of the base body 28 on which the adhesive layer 29 is formed. On the other hand, the inner electrode 27 is similarly formed on an inner surface of the base body 28 by vapor deposition or chemical plating or the like.

Subsequently, the electrode protection layer 100 is formed on the surface of the outer electrode 26 by a plasma spray that splays a heat-resistant ceramic, such as alumina-magnesia spinel.

Next, slurry is applied to the base body 28 on which the electrode protection layer 100 is formed and is dried to thereby form the poisoning prevention layer 101. The slurry for forming the poisoning prevention layer 101 is prepared by, for example, mixing predetermined quantity of titania powder, ceramic powder other than titania and alumina sol. The base body 28 on which the electrode protection layer 100 is formed is immersed in such slurry to thereby form a coating on the electrode protection layer 100. Further, the thus-coated base body 28 is dried to complete the poisoning prevention layer 101. As a result, the gas sensor element 2 is produced.

Figure 4:
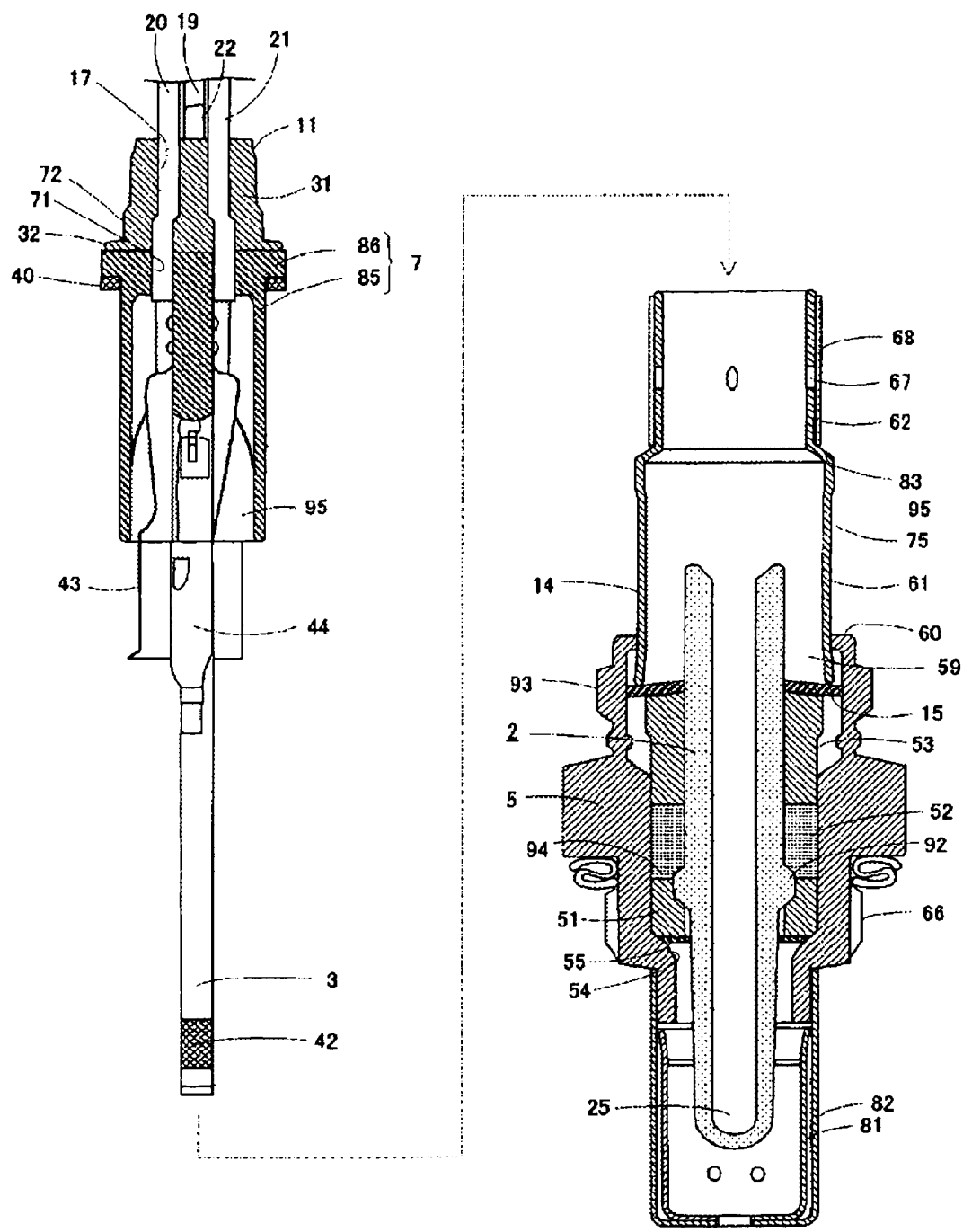
FIG. 4 is a sectional view for explaining an assembly method of an overall gas sensor.

Next, a method for manufacturing the gas sensor 1 in which the gas sensor element 2 is assembled will be described. First, as shown in FIG. 4, the leads for element 20 and 21 are joined to the terminal metal fittings 43 and 44, respectively, and the leads for heater 19 and 22 are joined to terminal metal fittings for heater of the ceramic heater 3. Then, while the ceramic heater 3 is disposed inside of the terminal metal fitting 44, the leads 19, 20, 21 and 22 are inserted, respectively, in the separator lead insertion holes 71 of the separator 7. Subsequently, while the leads 19, 20, 21 and 22 are inserted, respectively, in the lead insertion holes 17 of the elastic seal member 11, the front end face of the elastic seal member 11 is moved until being in contact with the rear end face of the separator 7. In this way, a sensor upper intermediate body is produced. In addition, the annular seal member 40 is provided around the outer circumference of the separator main body 85 beforehand.

The gas sensor element 2 is held in the metal shell 5, and the protectors 81 and 82 are welded to the front end side of the metal shell 5 to thereby separately assemble a sensor lower intermediate body which a front end side of the inner housing member 14 is connected to the rear end side of the metal shell 5. In addition, the cylindrical filter 68 is provided around the inner housing rear end side drum section 62 of the inner housing member 14.

The separator main body 85 of the separator 7 of the sensor upper intermediate body is located in the inner housing rear end side drum section 62 of the inner housing member 14 of the sensor lower intermediate body. In this way, the terminal metal fitting 44 is inserted in the closed-bottomed hole 25 of the gas sensor element 2 along with the ceramic heater 3 so as to be electrically connected to the inner electrode 27. Furthermore, the terminal metal fitting 43 is provided around the outer face of the gas sensor element 2 so as to be electrically connected to the outer electrode 26.

Figure 5:
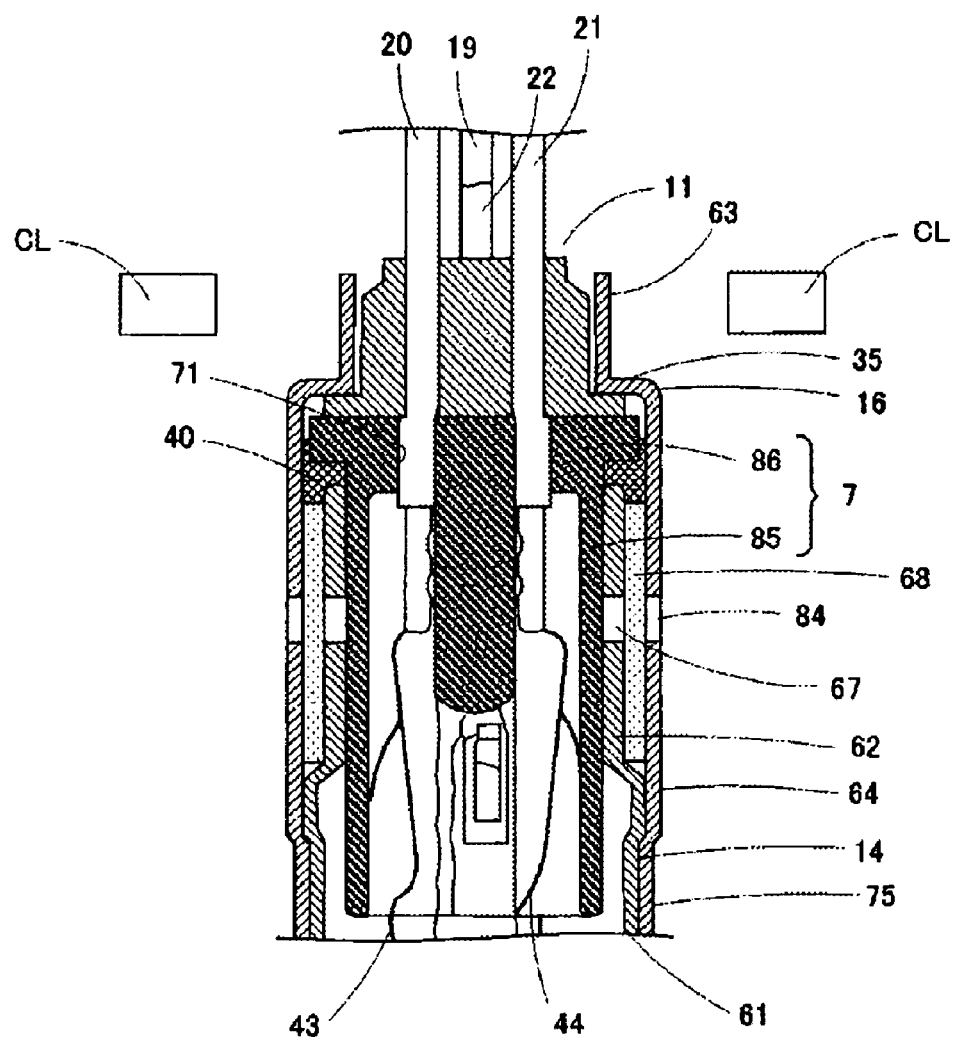
FIG. 5 is a sectional view for explaining an assembly method of a rear end side of a gas sensor.

As shown in FIG. 5, while each lead 19, 20, 21 and 22 are accommodated in the elastic seal member 11, the outer housing member 16 is moved from the rear end side of the elastic seal member 11 until it overlaps on the outside of the inner housing front end side drum section 61 of the inner housing member 14. Subsequently, while pressing the outer step portion 35 toward the front end side in the axis direction, the overlapped portion between the outer housing member 16 and the inner housing front end side drum section 61 is radially inwardly caulked to thereby form the coupled caulking portion 75. As a result, the outer housing member 16 and the inner housing member 14 are fixed together. This caulking portion is formed by round-caulking from all sides.

Furthermore, a portion of the outer housing member 16 (outer housing rear end side portion 63) which corresponds to the outer circumferential face of the elastic seal member 11 in the radial direction (i.e., the rear end portion of the outer housing rear end side portion 63) is radially inwardly caulked with a caulking jig CL so as to form the caulking portion 88. In this way, the elastic seal member 11 is compressed and deformed to thereby fix the elastic seal member 11 to the outer housing member 16 in an airtight manner. This caulking portion is also formed by round-caulking from all sides. Then, the outer housing member 16 fixed by the coupled caulking portion 75 and the inner housing member 14 are caulked to thereby form the first caulking portion 56 and the second caulking portion 57. As a result, the gas sensor 1 is completed.

Hereafter, the present invention will be described with reference to an embodiment.

The following tests were conducted in order to verify the effect of the present invention. First, the base body 28 in which the adhesive layer 29 used for manufacturing the gas sensor element 2 was formed with an appearance indicated in FIG. 1. That is, yttria with an amount indicated in a column of base body in the following Table 1 is added to zirconium oxide, and then alumina with an amount equivalent to the content as indicated in the column of base body in the following Table 1 is further added thereto. The resultant mixture was wet pulverized and then calcined at a temperature of 1300 degrees C. Thereafter, the obtained particles were again wet pulverized so as to obtain the fine material powder that has a particle size of not greater than 2.5 micrometers account for 90% or more of the entire material powder. An organic binder was added to a portion of the fine material powder, obtaining slurry. The obtained slurry was processed through use of a spray drier, producing granules having an average particle size of about 80 micrometers. Then, the thus-obtained granules were formed into the base body 28 (non-sintered body) having a cylindrical shape with one closed end.

Separately, yttria with the amount indicated in a column of adhesive layer in the following Table 1 is added to zirconium oxide, and alumina with an amount equivalent to the content as indicated in the column of adhesive layer in the following Table 1 is further added thereto. The resultant mixture was wet pulverized and then calcined at a temperature of 1300 degrees C. Thereafter, the obtained particles were again wet pulverized so as to obtain the fine material powder that has a particle size of not greater than 2.5 micrometers account for 90% or more of the entire material powder. An organic binder was added to the fine material powder, obtaining slurry. The obtained slurry was processed through use of a spray drier, producing granule having an average particle size of about 80 micrometers. Then, the fine material powder and the thus-obtained granules were mixed in a mixed ratio of 40:60 by weight to thereby obtain the roughening particles. Then, a mixed solvent of water and water-soluble binder $NH_4$—CMC is added to the roughening particles, producing the paste for forming the adhesive layer 29.

Next, the thus-produced paste was applied to the outer surface of the base body 28 (non-sintered body) with a thickness of 100 micrometers. The thus-coated base body 28 was sintered at a temperature of 1600 degrees C. for 1 hour under an oxidizing atmosphere. As a result, the base body 28 (sintered body) having the adhesive layer 29 was formed.

The proportion of tetragonal in zirconia particles (T phase), the average particle size ($ZrO_2$ diameter) of zirconia particles and the average particle size ($Al_2O_3$ diameter) of alumina particles of the base body 28 (sintered body) or the adhesive layer 29 of Embodiments 1-3 and the comparative samples 1 and 2 are shown in Table 1. The proportion of tetragonal (T phase), the average particle size of each particle shown in Table 1 were measured by the X-ray diffraction analysis and the scanning electron microscope (SEM), respectively, as already described in the above.

In addition, the proportion of tetragonal in zirconia particles (T phase) in the base body 28 (sintered body) or the adhesive layer 29 varied according to the amount of yttria added.

TABLE 1

| | Base Body | | | | | Adhesive Layer | | | | |
|---|---|---|---|---|---|---|---|---|---|---|
| | T Phase | ZrO$_2$ Particle Size | Y$_2$O$_3$ Content | Al$_2$O$_3$ Content | Al$_2$O$_3$ Particle Size | T Phase | ZrO$_2$ Particle Size | Y$_2$O$_3$ Content | Al$_2$O$_3$ Content | Al$_2$O$_3$ Particle Size |
| Embodiment 1 | 44% | 0.65 μm | 5.0 mol % | 11% | 0.8 μm | 60% | 0.55 μm | 4.4 mol % | 9% | 2 μm |
| Embodiment 2 | 54% | 0.45 μm | 4.6 mol % | 11% | 0.8 μm | 61% | 0.55 μm | 4.4 mol % | 9% | 2 μm |
| Embodiment 3 | 54% | 0.45 μm | 4.6 mol % | 11% | 0.8 μm | 58% | 0.50 μm | 4.5 mol % | 11% | 0.8 μm |
| Comparative Sample 1 | 63% | 0.55 μm | 4.4 mol % | 9% | 2 μm | 63% | 0.55 μm | 4.4 mol % | 9% | 2 μm |
| Comparative Sample 2 | 54% | 0.45 μm | 4.6 mol % | 11% | 0.8 μm | 54% | 0.45 μm | 4.6 mol % | 11% | 0.8 μm |

Next, a bending strength of the base body 28 in which the adhesive layer 29 was formed was measured. Further, bending strength was again measured after conducting a durability test that the base body 28 having the adhesive layer 29 was subjected to a heat treatment for 1000 hours with an excess coefficient λ=0.9 so that the temperature of the base body 28 reached at 300 degrees C. The result is shown in the following Table 2.

Figure 6:
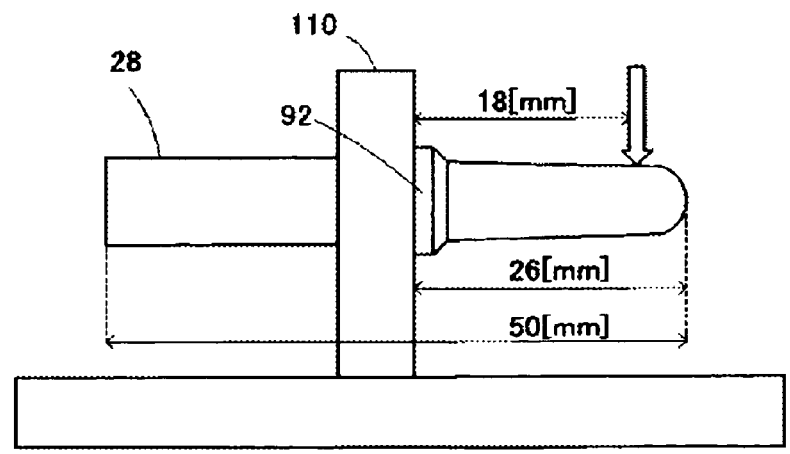
FIG. 6 is an outline showing a measuring method of a bending strength.

As shown in FIG. 6, the bending strength was measured in such a manner that the rear end side of the engaging flange portion 92 of the base body 28 having the adhesive layer 29 is fixed to a jig 110, and the maximum load was measured at a region 18 mm from the rear end side portion of the engaging flange portion 92. In addition, a full length of the base body 28 was 50 mm, and a length from the rear end side portion to the front end portion of the engaging flange portion 92 was 26 mm.

In Tables 1 and 2, "○" represents an "excellent" bending strength of over 0.30 [kN], "Δ" represents a "not so good" bending strength of more than 0.10 [kN] to below 0.30 [kN], and "X" represents a "poor" bending strength of below 0.1 [kN].

Further, the platinum electrode was formed by a conventionally known plating method on both outer surface side and inner surface side of the base body 28 having the adhesive layer 29 so as to form the outer electrode 26 and the inner electrode 27, respectively. Furthermore, the electrode protection layer 100 (spinel protection layer) and the poisoning prevention layer 101 were formed by a conventionally known method on the outer electrode 26 to thereby produce the gas sensor element 2. Then, TRL responsiveness of the gas sensor element 2 was measured. The result is shown in Table 2.

Figure 7:
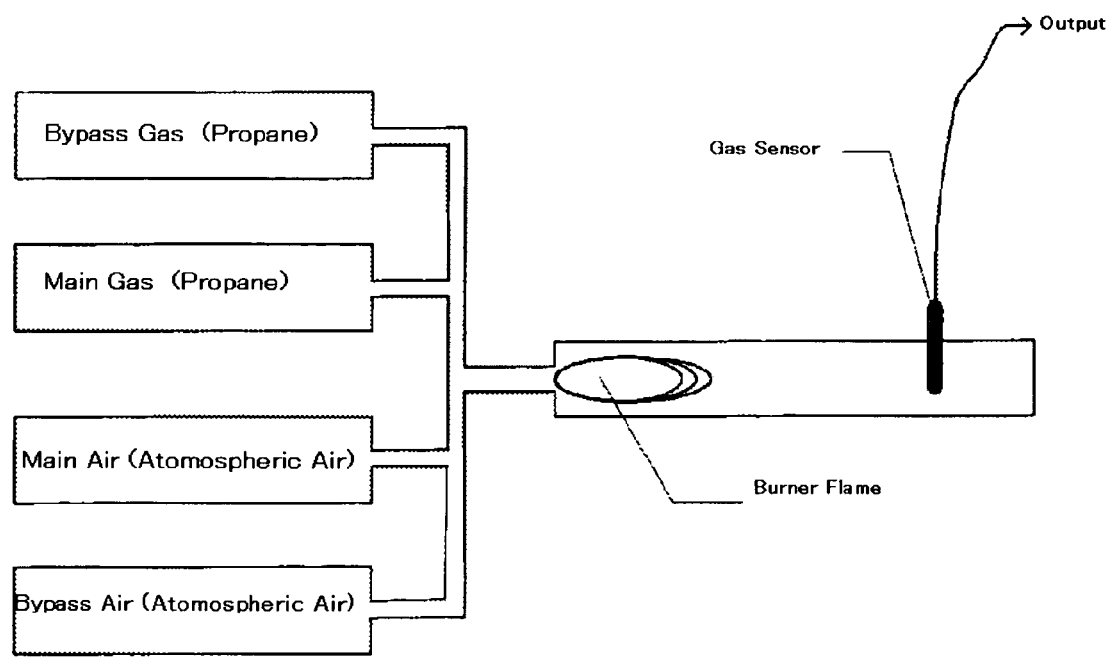
FIG. 7 is a schematic showing a burner measuring equipment used for measuring TRL responsiveness.

The TRL responsiveness was measure with a burner measuring apparatus shown in FIG. 7. After assembling the gas sensor element 2 on the burner measuring apparatus, a reference gas containing main propane and main air was combusted with a burner to produce a combustion atmosphere of λ=1. Based on the combustion atmosphere of λ=1, a composition of a combustion gas was adjusted using bypass propane and bypass air so that the combustion atmosphere was λ=0.9 to λ=1.1. When the combustion atmosphere was made to change from λ=0.9 to λ=1.1, the duration that an output of the sensor element 2 changed from 600 mV to 300 mV was measured. In Table 2, "○" represents an "excellent" responsiveness of 200 ms or less, and "x" represents a "poor" responsiveness of over 200 ms.

TABLE 2

| | Bending Strength | | TRL | Overall |
|---|---|---|---|---|
| | Initial Stage | Later Stage | Responsiveness | Evaluation |
| Embodiment 1 | 0.29 kN  Δ | 0.40 kN  ○ | 102 ms  ○ | Δ |
| Embodiment 2 | 0.40 kN  ○ | 0.70 kN  ○ | 105 ms  ○ | ○ |
| Embodiment 3 | 0.40 kN  ○ | 0.70 kN  ○ | 135 ms  ○ | ○ |
| Comparative Sample 1 | 0.42 kN  ○ | 0.10 kN  X | 101 ms  ○ | X |
| Comparative Sample 2 | 0.40 kN  ○ | 0.70 kN  ○ | 250 ms  X | X |

As it is apparent from Table 2, a comparative sample 1 in which the proportion of tetragonal in zirconia particles of the base body 28 was beyond the specified range of the present invention exhibited poor bending strength after the durability test of the base body 28. Further, a comparative sample 2 in which the proportion of tetragonal in zirconia particles of the base body 28 was within the specified range of the present invention, and in which the proportion of tetragonal in zirconia particles of the adhesive layer 29 was beyond the specified range of the present invention, exhibited sufficient bending strength after the durability test, however, TRL responsiveness was poor.

On the other hand, the embodiments 1-3 in which the proportion of tetragonal in zirconia particles of the base body 28 and that of tetragonal in zirconia particles of the adhesive layer 29 were within the specified range of the present invention exhibited sufficient bending strength and excellent TRL responsiveness both at the initial stage and after the durability test of the base body 28.

Furthermore, the alumina content in the base body 28 is preferably 10% or more by weight in order to exhibit excellent bending strength after the durability test. Furthermore, the average particle size of alumina particles of the base body 28 is preferably about 1 micrometer or less.

On the other hand, the proportion of tetragonal in zirconia particles of the adhesive layer 29 is preferably 60% or more because the TRL responsiveness can be about 100 ms. Further, the alumina content in the adhesive layer 29 is preferably 10% or less by weight in order to obtain excellent TRL responsiveness. Furthermore, alumina particles of the adhesive layer 29 preferably have the average particle size of 1.0 micrometers or more in order to obtain excellent TRL responsiveness.

The invention claimed is:
1. A gas sensor element, comprising:
    A closed-bottomed cylindrical base body made of solid electrolyte which contains zirconia as a principle component;
    An outer electrode formed on an outer surface of the base body;

An inner electrode formed on an inner surface of the base body; and

An adhesive layer formed between the base body and the outer electrode and containing zirconia as a principle component, Wherein the base body and the adhesive layer comprise tetragonal phase zirconia particles as well as other zirconia particles, Wherein a proportion of tetragonal in zirconia particles of the base body falls within a range from 45% or more to 60% or less, and Wherein a proportion of tetragonal in zirconia particles of the adhesive layer is greater than that of tetragonal in zirconia particles of the base body.

2. A gas sensor element according to claim 1, wherein a proportion of tetragonal in zirconia particles of the adhesive layer is 60% or more.

3. A gas sensor element according to claim 1 or 2, wherein the base body contains alumina of 5% by weight or more.

4. A gas sensor element according to claim 3, wherein an average particle size of alumina contained in the base body is 1 micrometer or less.

5. A gas sensor, comprising a gas sensor element and a metal shell which surrounds the gas sensor element, wherein the gas sensor employs the gas sensor element according to claim 1.

6. A gas sensor, comprising a gas sensor element and a metal shell which surrounds the gas sensor element, wherein the gas sensor employs the gas sensor element according to claim 2.

7. A gas sensor, comprising a gas sensor element and a metal shell which surrounds the gas sensor element, wherein the gas sensor employs the gas sensor element according to claim 3.

8. A gas sensor, comprising a gas sensor element and a metal shell which surrounds the gas sensor element, wherein the gas sensor employs the gas sensor element according to claim 4.

* * * * *